006c# United States Patent [19]

Nubel

[11] 4,014,742
[45] Mar. 29, 1977

[54] PRODUCTION OF CITRIC ACID IN SLACK WAX MEDIA
[75] Inventor: Robert C. Nubel, Wantagh, N.Y.
[73] Assignee: Pfizer Inc., New York, N.Y.
[22] Filed: Mar. 3, 1976
[21] Appl. No.: 663,347
[52] U.S. Cl. .......................... 195/28 R; 195/36 R; 195/37; 195/47
[51] Int. Cl.² .................................. C12D 1/04
[58] Field of Search ................ 195/28 R, 37, 36 R, 195/47

[56] References Cited
UNITED STATES PATENTS

| | | | |
|---|---|---|---|
| 3,271,266 | 9/1966 | Laine et al. | 195/3 R |
| 3,337,413 | 8/1967 | Wegner | 195/28 R |

OTHER PUBLICATIONS

Yoneyama et al., "Manufacture of Citric Acid", Cited in Chemical Abstracts 79:3852w (1973).

Primary Examiner—R. B. Penland
Attorney, Agent, or Firm—Connolly and Hutz

[57] ABSTRACT

Citric acid is produced by aerobically propagating a citric acid-accumulating strain of yeast of the genus Candida in an aqueous nutrient medium containing enough readily assimilable source of carbon to promote growth but insufficient to permit the accumulation of citric acid; introducing slack wax as the principal source of assimilable carbon together with a solubilizing agent into the aqueous nutrient medium after at least 50% of the readily assimilable source of carbon has been utilized, continuing the aerobic propagation until a level of at least about 1 gram of citric acid has been accumulated per liter of aqueous medium and recovering the citric acid, said solubilizing agent being selected from the group consisting of alkanols having 4 to 10 carbon atoms in each alkyl moiety, lower alkyl esters of alkanoic acids having 2 to 6 carbon atoms, alkenes and alkanes having 8 to 19 carbon atoms, turpentine, mineral oil and mixtures thereof.

5 Claims, No Drawings

PRODUCTION OF CITRIC ACID IN SLACK WAX MEDIA

BACKGROUND OF THE INVENTION

Because of its ease of assimilation, palatability and low toxicity, citric acid is one of the most widely used acids in the food and pharmaceutical industry. The acid is widely used as an acidulant in beverages and also as an antioxidant for inhibiting rancidity in fats and oils. Both the acid and its salts are employed as buffers in the preparation of jams, jellies and geltain preparations, and are also used as stabilizers in various food products.

Hitherto, citric acid fermentation processes have employed the use of selected strains of *Aspergillus niger* in aqueous nutrient media containing molasses, sucrose, dextrose, etc. as the principal source of assimilable carbon.

Recent developments described in Belgian Pat. No. 724,553, Japanese Pat. No. 20707 and U.S. Pat. No. 3,717,549 cover processes for the production of citric acid by the aerobic propagation of a citric acid-accumulating yeast in aqueous nutrient media containing carbohydrates as the principal source of assimilable carbon.

SUMMARY OF THE INVENTION

The present invention is concerned with a process for producing citric acid which comprises aerobically propagating a citric acid-accumulating strain of yeast of the genus Candida in an aqueous nutrient medium containing enough readily assimilable source of carbon to promote growth but insufficient to permit the accumulation of citric acid; introducing slack wax as the principal source of assimilable carbon together with a solubilizing agent into the aqueous nutrient medium after at least 50% of the readily assimilable source of carbon has been utilized, continuing the aerobic propagation until a level of at least about 1 gram of citric acid has been accumulated per liter of aqueous medium and recovering the citric acid, said solubilizing agent being selected from the group consisting of alkanols having 4 to 10 carbon atoms in each alkyl moiety, lower alkyl esters of alkanoic acids having 2 to 6 carbon atoms, alkenes and alkanes having 8 to 19 carbon atoms, turpentine, mineral oil and mixtures thereof.

DETAILED DESCRIPTION OF THE INVENTION

The present invention now provides a process for producing citric acid by aerobically propagating a citric acid-accumulating strain of a yeast of the genus Candida in an aqueous nutrient medium containing petroleum wax as the principal source of assimilable carbon.

Petroleum wax, known generically in the petroleum industry as slack wax, is a relatively homogeneous material consisting of long chain hydrocarbons having 20 to 30 carbon atoms. It is a solid substance at room temperature and has a freezing point of about 45° C. Slack wax is made from selected paraffin base lube oil fractions from the distillation units. Specifically, the oils are mixed with suitable solvents, chilled to form wax crystals, and then filtered to remove the wax from the mix. Further solvent treatment, solvent removal and treatment with steam produces the semi-refined wax that meets the requirements of FDA Food Additive Regulations subpart D & F Section 121.1156 and 121.2586.

There appears to be little current demand for the large amounts of slack wax that are produced as a by-product of the lube oil refining process; it is priced in about the same range as crude oil. There are no known literature reports or prior art references to the use of this material as a fermentation substrate for the production of microbial products.

The novelty of the present invention resides in the utilization of this solid, refractory hydrocarbon waste product as a readily available, inexpensive substrate for the production of citric acid by a citric acid-accumulating, hydrocarbon assimilating strain of a yeast belonging to the genus Candida. This is accomplished by first growing the Candida strain in an aqueous nutrient medium having a readily utilizable source of assimilable carbon so that a large mass of Candida cells can be obtained. This readily utilizable source of carbon may be glucose, a vegetable oil, a fatty acid ester or mixtures thereof, a normal paraffin having 9 to 19 carbon atoms or mixtures thereof or other suitable carbon sources known to those skilled in the art. The preferred carbon source is glucose at a concentration of 5 to 10% w/v, preferably 7.5% w/v. In addition, the medium contains a source of assimilable nitrogen such as ammonium nitrate, ammonium sulfate, ammonium chloride, wheat bran, soybean meal, urea, amino acids and peptones. It is, of course, well known that such vitamins as biotin and thiamine and such mineral cations and anions as sodium potassium, cobalt, phosphate and sulfate are also beneficial to the growth of yeasts.

The amount of readily assimilable source of carbon in the production medium is limited to that amount which is adequate for the growth of the added Candida cells but is insufficient to permit the accumulation of citric acid (less than 0.5 gram per liter). The upper concentration limit is fixed as that amount to which any incremental addition will permit the accumulation of citric acid (greater than 0.5 gram per liter). When glucose is used in the production medium, the concentration is 1 to 3% w/v, preferably 2% w/v.

The production fermentation is allowed to proceed for a period of time until at least 50%, and preferably 80%, of the glucose is assimilated (approximately 24 hours). An amount of slack wax is then added to provide a concentration of at least 3% by weight of the medium, preferably 5 to 20% by weight, along with a solubilizing agent. The addition of slack wax and solubilizing agent may be accomplished by adding all of the combination at one time or by additions at various times during the fermentation. For example, the first addition can be followed by similar additions at 24 hour intervals during the fermentation cycle.

Critical to the process of this invention is the use and selection of a suitable solubilizing agent for the slack wax. The solubilizing agent serves to dissolve or partially dissolve the slack wax so that it is made completely dispersable in the aqueous phase of the fermentation medium and so is made available to metabolic utilization by the growing Candida cells. The choice of the solubilizing agent is dependent on such factors as non-inhibitory action on the growing Candida cells, good solubility for slack wax, low volatility, low cost and ready availability. These criteria are met to one degree or another by alkanols having 4 to 10 carbon atoms in each alkyl moiety, lower alkyl esters of alkanoic acids having 2 to 6 carbon atoms, alkenes and alkanes having 8 to 19 carbon atoms, turpentine, mineral oil and mixtures thereof. A useful solubilizing agent is kerosene which is a mixture of petroleum hydrocarbons, chiefly of the methane series having from 10 to 16 carbon atoms per molecule. The amount or ratio of solubilizing agent to slack wax is dependent to some extent on the nature of the solubilizing agent but is generally in the range of 0.25:1 to 2:1. The preferred solubilizing agents are octane, nonane and decane in the ratio to slack wax of 1:1. This ratio may be varied during the fermentation additions but is generally maintained at the fixed level.

Since the slack wax and solubilizing agent are immiscible in the aqueous phase of the nutrient medium, it is desirable to maintain them in a finely dispersed form in the aqueous medium during the fermentation, thus insuring that a large surface of the materials will be in contact with the aqueous phase. In this manner there will be optimum contact between the yeast cells, the aqueous phase and the slack wax. A preferred means of accomplishing these objectives is submerged fermentation, rapidly stirring the mixture while simultaneously passing air through it, e.g., by sparging.

The usual temperatures known in the art for growing yeasts, e.g., about 20° to 37° C., may be employed, a range of from 25° to 29° C. being preferred with fermentation times of 4 to 7 days. The production fermentation is continued until at least about one gram of citric acid per liter of medium has been accumulated. The initial growth period of the yeast cells for preparation of the inoculum is preferably 24 to 48 hours. These general conditions of growth and fermentation are well known in the art, as are also methods for the recovery of the citric acid produced as the free acid, sodium salt or calcium salt by centrifugation, filtration, concentration under vacuum, etc.

Any of the known citric acid-accumulating strains of Candida is useful in the present invention and will provide varying levels of accumulated citric acid as the art appreciates. Suitable strains are available from various depositories around the world, and are identified in the earlier described foreign and United States patents. Illustrative strains include citric acid-accumulating strains of *Candida lipolytica*, *Candida guilliermondii*, *Candida tropicalis*, *Candida parapsilosis* and *Candida brumptii*. The preferred citric acid-accumulating strains are those belonging to the species *Candida lipolytica*. In accord with recent nomenclature practice, it is understood that the genus Candida is synonymous and interchangeable with the genus Saccharomycopsis.

Methods for the qualitative and quantitative determination of citric acid are described as follows, with pure reference samples of citric acid and isocitric acid as prerequisites. Gas Chromatography provides a sensitive method for differentiating and determining the amount of isocitric acid in the presence of citric acid.

METHODS OF ANALYSIS

I. Paper Chromatography

The systems below provide a convenient semiquantitative means for determining citric acid in the fermentation medium. Concentrations of citric acid even lower than 1 gram per liter of medium, i.e., 1 mg. per ml. of medium can be readily detected by these chromatographic methods.

1. Solvent System A

This solvent system is a mixture by volume of 80 parts methyl ethyl ketone, 6 parts acetone, 12 parts distilled water and 2 parts formic acid. Citric acid exhibits an $R_f$ of about 0.59 to 0.64 with this system.

2. Solvent System B

This solvent system consists of by volume 1 part formic acid, 2 parts cineole, and 3 parts n-propanol. The Rf of citric acid with this system is about 0.40 to 0.45.

3. Solvent System C

This solvent system consists of a water-saturated formic acid-ether mixture prepared by shaking together in a separatory funnel a mixture consisting of 2100 ml. of ethyl ether, 300 ml. of formic acid, and 275 ml. of water. After shaking, the upper solvent layer is used as the chromatographic solvent. The Rf of citric acid with this system is about 0.30 to 0.35.

A 5 to 10 microliter sample of the aqueous phase of the effluent, which had been separated from the fermentation medium as described above, is dried at 80° C in vacuo to convert any isocitric acid to the lactone, redissolved in water and placed on the paper, and the chromatogram run in the usual manner. We generally use Whatman No. 1 paper as the absorbent and Bromocresol Green as the indicator (prepared by dissolving 0.25 g. of Bromocresol Green in 400 ml. of acetone and adjusting the solution to green color) in these analyses. In all cases an authentic sample of citric acid is run with each chromatogram as a standard.

II. Pentabromoacetone Analysis

Various methods involving the formation of pentabromoacetone can be used for determining citric acid in the presence of isocitric acid. One preferred method is that described by H.A. Krebs in Biochem. J. 54, 78 (1953) and in Methods in Enzymology, volume XIII, edited by J. M. Lowenstein, p. 515.

III. Gas Chromatography

This is another quantitative method for determining citric and isocitric acids that we have used. The analysis is carried out with a Pye model 104 gas chromatograph fitted with a flame ionization detector under the following conditions:

Column—Glass, 7' × ¼" pack with 3% OV17 on Chrom W(HP)
Column T—140°–150° C
Detection block T—230° C
Helium flowrate—50 ml/min.
Hydrogen flowrate—50 ml/min.
Air flowrate—500 ml/min.
Sample size—10 microliters A standard sample is prepared by first weighing out exactly 60 mg. of anhydrous citric acid and 1.8 mg. of isocitric acid. This is dissolved in 3.0 ml. of tetrahydrofuran (THF) and 20 $\mu$l of sulfuric acid is added, followed by 1.0 ml. of N,O-bis (trimethylsilyl)acetamide (BSA). The mixture is then heated to 60° C for 1 hour and a 10$\mu$l portion is injected into the gas chromatograph. The chromatogram thus obtained shows peaks corresponding to citric acid and isocitric acid and the areas under the peaks are conveniently calculated by means of an integrator attached to the Gas Chromatograph.

A sample of the aqueous phase of effluent, separated from the fermentation medium, is then taken and 1.0 ml. is freeze dried for at least 4 hours. To the dry residue are added 10 ml. of THF, 100 $\mu$l of sulfuric acid and 10 glass balls. The mixture is shaken vigorously to ensure dissolution of the dry residue, 3.0 ml. of the solution are transferred to a glass vial, 1.0 ml. of BSA is added and the mixture treated and submitted to gas chromatography exactly as described for the standard above. The amounts of citric acid and isocitric acid in the sample are readily calculated by comparison of the chromatogram obtained with that obtained for the standard.

EXAMPLE I

Cells of *Candida lipolytica* NRRL Y-1094 grown on a potato dextrose agar slant are inoculated into a Fernbach flask containing 800 ml of sterile medium having the following composition.

| Ingredient | Grams/liter |
|---|---|
| Glucose | 75.0 |
| $MgSO_4.7H_2O$ | 0.25 |
| $KH_2PO_4$ | 0.50 |
| Calcium phytate | 0.50 |
| $(NH_4)_2SO_4$ | 4.0 |
| $CaCO_3$ | 5.0 |
| Yeast extract | 1.0 |

The inoculated flask is incubated at 26° C. on a rotary shaker for 48 hours after which a 100 ml portion of the grown culture (first stage inoculum) is aseptically transferred to a 4 liter fermentor containing 2 liters of sterile medium having the same composition as that used in the Fernbach flask. The fermentor is stirred at 1750 rpm and air is introduced through a sparger at the rate of 4 standard cubic feet per hour per gallon of medium. The temperature is maintained at 26° C.

The fermentation in the fermentor is continued for 72 hours at which time 100 ml portions (second stage inoculum) are transferred to a series of identical fermentors, each containing 2 liters of sterile medium of the following composition:

| Ingredient | Grams/liter |
|---|---|
| Glucose | 20.0 |
| Thiamine hydrochloride | 0.001 |
| $MgSO_4.7H_2O$ | 0.20 |
| $CaCO_3$ | 17.0 |
| Urea | 4.05 |
| $KH_2PO_4$ | 0.75 |

Fermentation is allowed to proceed for 24 hours at which time 100 ml of liquefied slack wax (Moore & Munger, Inc., Stamford, Conn.) is added to one of the fermentors. Similarly, 100 ml of n-octane is added to a second fermentor, and to a third fermentor is added 100 ml of n-octane and 100 ml of slack wax. Identical additions are made to each fermentor at 48 hours, 72 hours and 96 hours. The fermentation in each fermentor is allowed to proceed for a total of 137 hours.

| Additions | Grams of Citric Acid per Fermentor |
|---|---|
| n-octane | none |
| slack wax | none |
| n-octane + slack wax | 5.44 |

EXAMPLE II

The method of Example I may be repeated with comparable results replacing glucose with soybean oil, peanut oil, butyl ester of oleic acid and glyceryl ester of linoleic acid.

EXAMPLE III

The method of Example I may be repeated with comparable results replacing n-octane with turpentine, kerosene, mineral oil, butanol, amyl alcohol, octanol, decanol, ethyl acetate and butyl hexanoate.

EXAMPLE IV

The method of Example I is repeated with n-nonane in place of n-octane with the following results:

| Additions | Grams of Citric Acid per Fermentor |
|---|---|
| n-nonane | none |
| slack wax | none |
| n-nonane + slack wax | 73.61 |

EXAMPLE V

The method of Example I is repeated with n-decane in place of n-octane with the following results:

| Additions | Grams of Citric Acid per Fermentor |
|---|---|
| n-decane | 5.37 |
| slack wax | none |
| n-decane + slack wax | 181.15 |

EXAMPLE VI

The method of Example V may be repeated with comparable results with n-decane to slack wax ratios of 0.25:1 and 2:1.

EXAMPLE VII

The method of Example I is repeated with n-dodecane in place of n-octane with the following results:

| Additions | Grams of Citric Acid per Fermentor |
|---|---|
| n-dodecane | 153.51 |
| slack wax | none |
| n-dodecane + slack wax | 208.40 |

EXAMPLE VIII

The method of Example VII may be repeated with comparable results replacing n-dodecane with a mixture of n-alkenes and n-alkanes of 9 to 19 carbon atoms.

EXAMPLE IX

The method of Example VI may be repeated with comparable results utilizing in turn each of the following citric acid-accumulating strains of Candida:

| | |
|---|---|
| *Candida lipolytica* | ATCC 8662 |
| *Candida lipolytica* | ATCC 9773 |
| *Candida lipolytica* | ATCC 20114 |
| *Candida lipolytica* | ATCC 20182 |
| *Candida tropicalis* | ATCC 20115 |
| *Candida intermedia* | ATCC 20178 |
| *Candida parapsilosis* | ATCC 20181 |
| *Candida guilliermondii* | ATCC 20118 |
| *Candida brumptii* | ATCC 20117 |

What is claimed is:

1. A process for producing citric acid which comprises aerobically propagating a citric acid accumulating strain of yeast of the genus Candida in an aqueous nutrient medium containing enough readily assimilable source of carbon to promote growth but insufficient to permit the accumulation of citric acid; introducing slack wax as the principal source of assimilable carbon together with a solubilizing agent into the aqueous nutrient medium after at least 50% of the readily assimilable source of carbon has been utilized, continuing the aerobic propagation until a level of at least about 1 gram of citric acid has been accumulated per liter of aqueous medium and recovering citric acid, said solubilizing agent being selected from the group consisting of alkanols having 4 to 10 carbon atoms in each alkyl moiety, lower alkyl esters of alkanoic acids having 2 to 6 carbon atoms, alkenes and alkanes having 8 to 19 carbon atoms, turpentine, mineral oil and mixtures thereof.

2. The process of claim 1 wherein said readily assimilable source of carbon is glucose.

3. The process of claim 1 wherein said solubilizing agent is n-alkane having 8 to 12 carbon atoms.

4. The process of claim 1 wherein said solubilizing agent is n-decane.

5. The process of claim 1 wherein the ratio of solubilizing agent to slack wax is from 0.25:1 to 2:1.

* * * * *